United States Patent [19]

Shepard

[11] 4,126,904

[45] Nov. 28, 1978

[54] ARTIFICIAL LENS AND METHOD OF LOCATING ON THE CORNEA

[76] Inventor: Dennis D. Shepard, 1414 S. Miller St., Santa Maria, Calif. 93454

[21] Appl. No.: 783,300

[22] Filed: Mar. 31, 1977

[51] Int. Cl.² .......................... A61F 1/16; A61F 1/24; G02C 7/04
[52] U.S. Cl. ...................................... 3/13; 351/160 R
[58] Field of Search ......................... 3/13, 1; 351/160

[56] References Cited

U.S. PATENT DOCUMENTS

| | | | |
|---|---|---|---|
| 1,782,331 | 11/1930 | Wilhelm | 351/160 |
| 2,653,515 | 9/1953 | Stimson | 3/13 UX |
| 3,074,407 | 1/1963 | Moon et al. | 3/13 X |
| 3,228,741 | 1/1966 | Becker | 3/13 X |
| 3,246,941 | 4/1966 | Moss | 351/160 |

*Primary Examiner*—Ronald L. Frinks
*Attorney, Agent, or Firm*—Fulwider, Patton, Rieber, Lee & Utecht

[57] ABSTRACT

An artificial lens and method of locating the lens on the cornea. The optical portion is adapted for location on the central anterior corneal surface and is dimensioned to overlie substantially less than the total surface area of the cornea. The haptic portion is adapted for fixation to the cornea or an adjacent portion of the eyeball. In a preferred embodiment the haptic portion comprises a pair of ribbons or tabs superiorly and inferiorly attached to the cornea periphery. The lens moves with the cornea and is small enough that satisfactory corneal oxygenation is obtained. Various embodiments of the lens enable various types of attachment to the eyeball.

14 Claims, 10 Drawing Figures

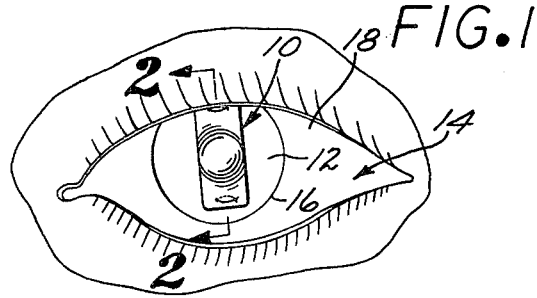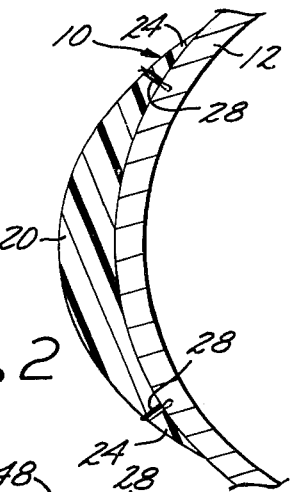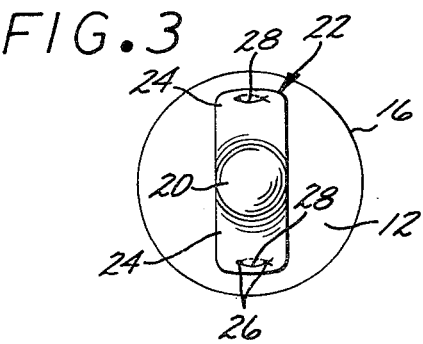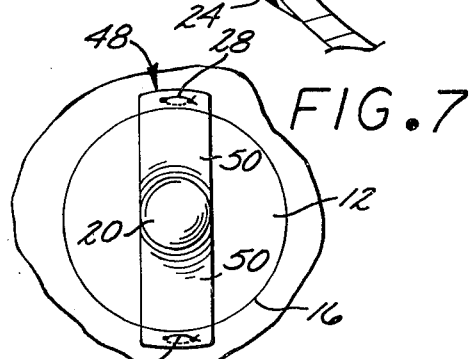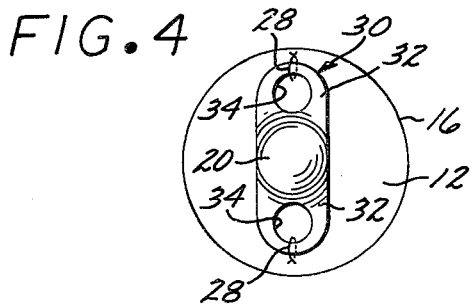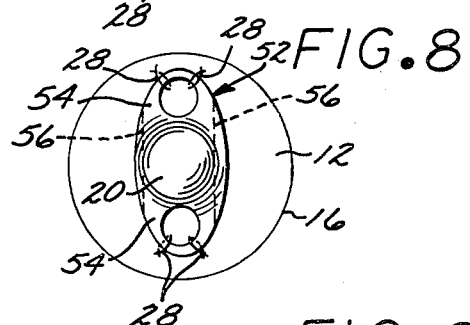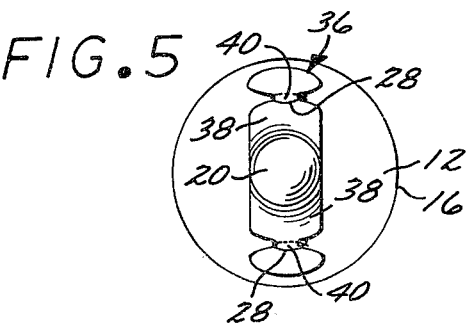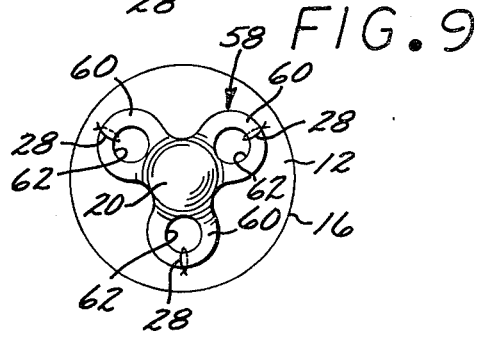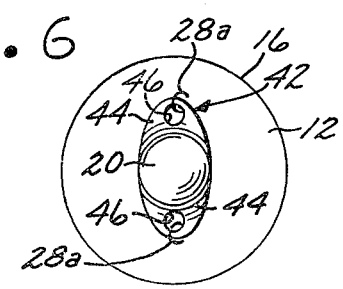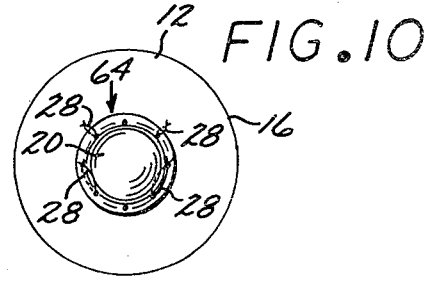

ARTIFICIAL LENS AND METHOD OF LOCATING ON THE CORNEA

BACKGROUND OF THE INVENTION

1. Field of the Invention

The present invention relates to an artificial lens for eyes and a method of locating the lens on the cornea, and particularly to a lens and method for fixation of the lens to the eyeball.

2. Description of the Prior Art

Contact lens adapted to fit over the cornea of the eye are well known in the prior art. They are made from so-called "hard" materials which are generally inflexible and typically 8½ to 9 millimeters in diameter. The relatively large diameter of the lens results in eye irritation after prolonged periods of wearing. The cornea requires continuous oxygen replenishment and continuous removal of carbon dioxide concentrations. The tear film washing over the corneal surface normally accomplishes this. However, the relatively large contact lens covering the cornea interferes with this function of the tear film. Various attempts have been made to reduce the amount of the lens in actual contact with the cornea, such as by cutting openings or fenestrating the lens, or by undercutting the margins of the lens. This has been successful only to a limited extent.

So-called "soft" are made of a material generally conformable to the curvature of the individual cornea. They are therefore characterized by less irritation. In addition, the lens material is relatively porous and provides a degree of lubrication and tearing not possible with a hard lens. The gas permeable character of the lens material also promotes oxygenation of the corneal surface and removal of carbon dioxide concentrations. However, such soft lenses tend to harbor and promote growth of undesirable bacteria, and scrupulous care must be exercised to maintain the soft lens in a sterile condition to avoid eye irritation.

The foregoing lens types are typical of prior art attempts to provide a lens large enough to utilize the spherical surface of the cornea for self-centering adjacent the pupillary zone of the cornea, and with provision for tear film access to the corneal surface underlying the lens. Enlargement of the lens surface to enhance self-centering of the lens usually results in eye irritation, while any significant reduction of the lens surface area achieves improved tearing of the corneal surface at the expense of proper optical positioning of the lens.

Neither soft nor hard lenses are normally designed to maintain a fixed rotative position relative to the eye. Consequently, it is difficult to grind the lens to correct for astigmatism along a diametral axis of the lens. Various means have been attempted which tend to prevent a lens from rotating, such as by having the lower margin of the lens ground to provide a chord adapted to ride against the lower eyelid, or by weighting of the lens so that a particular portion is always oriented downwardly, but such lenses have met with only limited success.

SUMMARY OF THE INVENTION

According to the present invention, an artificial lens is provided which is sufficiently small that the limited corneal surface covered by the lens can be adequately oxygenated by lateral diffusion, and accumulations of carbon dioxide similarly carried away. The lens is attached in position by fastening means which permanently secure the lens to the eyeball. More particularly, the present lens comprises a lens or optical portion configured for placement upon a relatively small section of the central anterior corneal surface. The lens includes a marginal or haptic portion which extends from the optical portion and includes a means enabling fixation of the haptic portion to the eyeball.

In certain embodiments the haptic portion comprises a plurality of radially outwardly extending ribbons or tabs which can be stapled or sutured to the cornea, or which are made long enough that they can be superiorly and inferiorly attached to the episclera.

The haptic portion in certain embodiments is provided with openings through which sutures can be disposed. In other embodiments the haptic portion is notched to provide suitable anchorages for sutures or like fastener elements.

The area of the optical portion of the lens approximates the area of the maximum pupillary opening, which is considerably less than the area of prior art hard or soft contact lenses. The width of the haptic portion of the lens is preferably the same as or less than the width of the optical portion to minimize the corneal surface covered by the complete lens structure.

The method of the invention contemplates suturing, stapling, or like attachment means for securing the lens to adjacent structure of the eyeball so that the lens moves with the eyeball.

Other objects and features of the invention will become apparent from consideration of the following description taken in connection with the accompanying drawings.

BRIEF DESCRIPTION OF THE DRAWINGS

FIG. 1 is a front elevational view of a human eye, illustrating the present lens in position upon the cornea;

FIG. 2 is an enlarged view taken along the line 2—2 of FIG. 1;

FIG. 3 is a front elevational view of the cornea, illustrating the present artificial lens in position;

FIG. 4 is a view similar to FIG. 3, but illustrating a second embodiment of the artificial lens;

FIG. 5 is a view similar to FIG. 3, but illustrating a third embodiment of the artificial lens;

FIG. 6 is a view similar to FIG. 3, but illustrating a fourth embodiment of the artificial lens;

FIG. 7 is a view similar to FIG. 3, but illustrating a fifth embodiment of the artificial lens which is characterized by tab or ribbon portions sufficiently long to enable attachment of their extremities to the episclera adjacent the cornea;

FIG. 8 is a view similar to FIG. 3, but illustrating a sixth embodiment of the artificial lens;

FIG. 9 is a view similar to FIG. 3, but illustrating a seventh embodiment of the artificial lens; and FIG. 10 is a view similar to FIG. 3, but illustrating an eighth embodiment of the artificial lens.

DESCRIPTION OF THE PREFERRED EMBODIMENT

Referring now to the drawings, and particularly to FIGS. 1 through 3, there is illustrated an artificial lens 10 for eyes. The lens 10 is illustrated in position upon the cornea 12 of the eyeball 14. The outer margin or limbus of the corneal area is generally designated by the numeral 16, beyond which is located the white sclera 18.

The lens 10 comprises a lens or optical portion 20 which is preferably circular and dimensioned to overlie the pupillary zone. The area of the optical portion 20 approximates the area of the maximum pupillary opening, that is, the outer margin of the optical portion overlies the maximum opening defined by the iridio-pupillary margin. This is sufficient to provide satisfactory vision and is significantly less than the total anterior surface area of the cornea normally covered by the usual prior art hard or soft contact lens. The average pupillary diameter under normal lighting conditions is approximately 3 millimeters, and under reduced lighting conditions is approximately 5 millimeters. A preferred diameter for the optical portion is therefore 5 to 6 millimeters. In contrast, prior art "hard" lenses are approximately 8½ to 9 millimeters in diameter, while "soft" lenses are approximately 13 millimeters.

The lens 10 also includes an integral marginal or haptic portion 22. The term "haptic" is intended to denote the non-optical portion of the lens 10. It affords a means for fixation of the lens 10 to the eyeball 14. In the embodiment illustrated in FIGS. 1 through 3, the haptic portion 22 includes a pair of ribbons or tabs 24 extending radially outwardly of the optical portion 20 and characterized by a width approximating the diameter of the optical portion 20. The length of the tabs 24 is such that their free ends overlie the sclera 18 adjacent the corneal boundary 16. The relatively small size of the lens 10 allows satisfactory corneal oxygenation and removal of carbon dioxide concentrations. Additionally, optical portion 20 may be fenestrated to allow even more transfer of oxygen and carbon dioxide.

The optical portion 20 is made of the appropriate dioptic power and posterior curvature to fit over the cornea 12. As best seen in FIG. 2, it constitutes the enlarged central portion of the lens 10 and its juncture with the thinner tabs 24 is of gradually diminishing thickness to eliminate any abrupt changes in shape which might be a cause of eye irritation. Likewise, the side and end margins of the portion 20 and tabs 24 are outwardly feathered or made of gradually dimishing cross section to enable smooth passage of the eyelid over the lens 10.

The tabs 24 include a means which enables complete fixation of the lens 10 to the eyeball 14. Such means comprise apertures or openings 26 in the free extremities of the tabs 24 adapted to receive fastening elements such as surgical sutures 28 which preferably extend into the underlying tissue of the cornea 12 to a depth of approximately ½ millimeter. The cornea is approximately 1 milimeter in thickness in this area. Usual surgical procedures are employed to effect placement of the sutures, as by initially applying a topical anesthetic and thereafter employing usual microscopic or operating loupes to precisely locate the sutures superiorly and inferiorly in the peripheral cornea, as illustrated.

The material of the lens may be selected from any of the various lens materials available. If materials such as are common in the prior art "soft" contact lens are used, the suturing should preferably be done with a cutting needle to form the desired openings 26 in the tabs 24 during the suturing procedure. In the event that a so-called "hard" lens material is used such as polymethylmethacrylate, the openings 26 should first be drilled or otherwise formed.

The sutures 28 must be biologically inert and resistant to absorption or deterioration by human body fluids. Either metallic or plastic materials can be used, as will be apparent to those skilled in the art, including Nylon, Supramid, polypropylene, stainless steel, or platinum-iridium wire.

The just-described method of locating the lens 10 on the cornea 12 provides what might be termed a "permanent" contact lens installation. The lens does not have to be removed, which is a matter of great convenience for wearers suffering from arthritis or similar disabling ailments which make it difficult to handle a contact lens. In the event that it should become necessary to remove the lens 10, the sutures 28 are simply cut and the lens is separated from the cornea. No impairment of vision should occur and the cornea heals relatively quickly.

The complete fixation of the lens 10 on the eyeball 14 permits the optical portion 20 to be ground to correct for astigmatism along a predetermined diametral axis. The non-rotatability of the optical portion 20 insures that any correction for astigmatism continues to be effective.

In FIG. 4 there is illustrated a haptic portion 30 which comprises a pair of ribbons or tabs 32 which each include a relatively large opening 34 in their free extremities. The openings 34 provide attachment points for the sutures 28 but are additionally important to provide exposure of more of the cornea 12 to the usual tear film.

FIG. 5 illustrates a haptic portion 36 comprising a pair of ribbons or tabs similar to the tabs 34 of FIG. 3, but characterized by notches defining areas 40 of reduced width to provide anchorages for the sutures 28. The areas 40 also expose more of the cornea to the action of the tear film.

FIG. 6 illustrates yet another embodiment of the present lens. This embodiment employs a haptic portion 42 characterized by a pair of ribbons or tabs 44 similar to the tabs 24 of FIG. 3, but with larger openings 46. Instead of sutures, usual and conventional Anis staples 28a can be used. The ends of the tabs 44 are of diminished width to increase the area of the cornea exposed to the tear film, as compared to the area of the tabs 24 of FIG. 3.

FIG. 7 illustrates another embodiment in which a haptic portion 48 is defined by a pair of ribbons or tabs 50 similar to the tabs 24 of FIG. 3, but of greater length to locate their free ends outside the corneal boundary 16 and in overlying relation to the sclera 18. The sutures 28 are disposed through the episclera to fix the lens 10 in the illustrated position.

FIG. 8 illustrates yet another embodiment of the invention, the haptic portion 52 being characterized by a pair of ribbons or tabs 54 configured essentially like the tabs 44 of the embodiment of FIG. 6. However, the central portions of the tabs 54 are wider than the optical portion 20, becoming progressively narrower toward their free ends. In addition, the tabs 54 are undercut or beveled, as indicated by the dotted lines 56, to increase the area of the cornea 12 exposed to the tear film.

FIG. 9 illustrates a haptic portion 58 characterized by three radially outwardly extending ribbons or tabs 60 provided with relatively large suture openings 62. All three tabs 60 are sutured to the cornea 12, as illustrated.

In FIG. 10 there is illustrated a lens having a haptic portion 64 comprising an annular section surrounding the optical portion 20 and secured to the cornea 12 by a plurality of generally equally circumferentially spaced sutures 28, preferably both single and mattress type sutures.

The method of locating the lens 10 on the cornea 12 comprises the steps of applying a lens 10 to the anterior surface of the cornea 12, the lens 10 having a posterior surface curvature complemental to such anterior surface. Next, the optical portion 20 of the lens is centered to overlie the pupillary zone of the cornea and the haptic portion 22 is attached to the eyeball 14 to fix it in position. In one method the haptic portion 22 is stapled or sutured to superiorly and inferiorly located peripheral portions of the cornea, while in another method the haptic portion 22 is fixed to the episclera immediately adjacent the corneal boundary. The sutures or other attachment means pass through one or more layers of the cornea. The sutures or staples are not tied or locked so tightly as to cause an alteration of the corneal curvature and thereby induce astigmatism.

The contact lenses of the prior art have been designed to move relative to the cornea to allow the tear film to reach almost all portions of the cornea beneath the lens. Great care has been exercised to promote such movement. In contrast, the present lens 10 is designed for the opposite purpose of fixing it to the cornea so that no relative movement is possible. This surprising departure from the prior art is possible primarily because of the drastic reduction in the size of the lens. The reduced lens area greatly improves metabolism and minimizes concentrations of foreign bodies such as bacteria and inorganic debris. Consequently, it can be worn indefinitely without significant eye irritation.

In practicing the present invention it is of primary importance to reduce the size of the lens as much as possible, commensurate with the object of providing an optical portion sufficiently large to provide the desired optical corrections, and a haptic portion adapted to be secured to the eyeball and preferably the cornea. However, the particular lens configuration, lens materials, attachment means or the like that are used is a matter of choice and are not critical to the present invention. Alternative structures and materials for accomplishing the stated functions will immediately suggest themselves to those skilled in the art, and are within the intended scope of the invention.

Various modifications and changes may be made with regard to the foregoing detailed description without departing from the spirit of the invention.

I claim:

1. An artificial lens for eyes, said lens comprising:
    an optical portion configured for placement upon the central anterior surface of the cornea, said optical portion being dimensioned to overlie less than the total anterior surface area of the cornea; and
    a marginal haptic portion extending from said optical portion and including means adapted to extend through a portion of the eyeball for fixation of said haptic portion to the eyeball.

2. An artificial lens according to claim 1 wherein said haptic portion comprises a pair of oppositely extending tabs each having a width approximating the width of said optical portion.

3. An artificial lens according to claim 1 wherein said haptic portion is annular, and said means comprise openings adapted to receive fastening elements.

4. An artificial lens according to claim 1 wherein said haptic portion comprises a pair of oppositely extending tabs each having a width approximating the width of said optical portion, and each having a length such that their outer extremities are adapted to overlie a portion of the sclera for fixation to the sclera.

5. An artificial lens according to claim 1 wherein said haptic portion is undercut to reduce its potential area of contact with the cornea.

6. An artificial lens for eyes, said lens comprising:
    an optical portion configured for placement upon the central anterior surface of the cornea, said optical portion being dimensioned to overlie less than the total anterior surface area of the cornea; and
    a marginal haptic portion including a plurality of tabs extending from said optical portion, said tabs having openings adapted to receive fastening elements.

7. An artificial lens according to claim 6 wherein said openings are relatively large to reduce the potential area of contact with the cornea.

8. An artificial lens for eyes, said lens comprising:
    an optical portion configured for placement upon the central anterior surface of the cornea, said optical portion being dimensioned to overlie less than the total anterior surface area of the cornea; and
    a marginal haptic portion including a plurality of tabs extending from said optical portion, said tabs having notches adapted to serve as anchorages for fastener elements.

9. An artificial lens for eyes, said lens comprising:
    an optical portion configured for placement upon the central anterior surface of the cornea, said optical portion having a posterior surface curvature complementary to the anterior surface curvature of the cornea for direct contact therewith, said optical portion being dimensioned to overlie less than the total anterior surface of the cornea; and
    a marginal haptic portion extending from said optical portion and including means enabling fixation of said haptic portion to the eyeball.

10. A method of locating on the cornea an artificial lens provided with an optical portion having a posterior surface area substantially less than the anterior surface area of the cornea and characterized by a curvature complemental to such anterior surface, and further provided with a marginal haptic portion extending outwardly of said optical portion, comprising the following steps:
    applying said artificial lens to the anterior surface of the cornea and arranging said optical portion to overlie the pupillary central zone of the cornea; and
    attaching said haptic portion to the portion of the eyeball adjacent said haptic portion by means extending through a portion of the eyeball to fix said optical portion upon the cornea for movement therewith.

11. A method of locating on the cornea an artificial lens provided with an optical portion having a posterior surface area substantially less than the anterior surface area of the cornea and characterized by a curvature complemental to such anterior surface, and further provided with a marginal haptic portion extending outwardly of said optical portion, comprising the following steps:
    applying said artificial lens to the anterior surface of the cornea and arranging said optical portion to overlie the pupillary central zone of the cornea; and
    attaching said haptic portion to the portion of the eyeball adjacent said haptic portion by passage of surgical staples through one or more layers of said cornea and coupling of said staples to said haptic portion to fix said optical portion upon the cornea for movement therewith.

12. A method of locating on the cornea an artificial lens provided with an optical portion having a posterior surface area substantially less than the anterior area of the cornea and characterized by a curvature complemental to such anterior surface, and further provided with a marginal haptic portion extending outwardly of said optical portion, comprising the following steps:

applying said artificial lens to the anterior surface of the cornea and arranging said optical portion to overlie the pupillary central zone of the cornea; and attaching said haptic portion to the portion of the eyeball adjacent said haptic portion by passage of surgical sutures through one or more layers of said cornea and through openings in said haptic portion to fix said optical portion upon the cornea for movement therewith.

13. A method according to claim 12 wherein said surgical sutures are passed through superiorly and inferiorly located peripheral portions of the cornea.

14. An artificial lens for eyes, said lens comprising:

an optical portion configured for placement upon the central anterior surface of the cornea, said optical portion being dimensioned to overlie less than the total anterior surface area of the cornea; and a marginal haptic portion including a plurality of tabs extending from said optical portion and having openings formed by the passage of fastening elements through said tabs.

* * * * *

UNITED STATES PATENT AND TRADEMARK OFFICE
CERTIFICATE OF CORRECTION

PATENT NO. : 4,126,904
DATED : November 28, 1978
INVENTOR(S) : DENNIS D. SHEPARD It is certified that error appears in the above-identified patent and that said Letters Patent are hereby corrected as shown below:

IN THE SPECIFICATION:

Column 1, line 28, after "soft" insert --lenses--;

Column 3, line 51, delete "milimeter" and substitute therefor --millimeter--.

Signed and Sealed this

First Day of May 1979

[SEAL]

Attest:

RUTH C. MASON
Attesting Officer

DONALD W. BANNER
Commissioner of Patents and Trademarks